US009289450B2

(12) United States Patent
Burton et al.

(10) Patent No.: US 9,289,450 B2
(45) Date of Patent: Mar. 22, 2016

(54) SILVER-CONTAINING ANTIMICROBIAL ARTICLES AND METHODS OF MANUFACTURE

(75) Inventors: Scott A. Burton, Woodbury, MN (US); David R. Holm, Hudson, WI (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 13/461,163

(22) Filed: May 1, 2012

(65) Prior Publication Data

US 2012/0237584 A1   Sep. 20, 2012

Related U.S. Application Data

(62) Division of application No. 12/160,439, filed as application No. PCT/US2007/000594 on Jan. 10, 2007, now Pat. No. 8,192,764.

(51) Int. Cl.
| | | |
|---|---|---|
| *A61L 15/18* | (2006.01) | |
| *A61K 33/38* | (2006.01) | |
| *A01N 59/16* | (2006.01) | |
| *A61L 2/08* | (2006.01) | |
| *A61L 2/238* | (2006.01) | |
| *A61L 15/46* | (2006.01) | |

(52) U.S. Cl.
CPC .............. *A61K 33/38* (2013.01); *A01N 59/16* (2013.01); *A61L 2/08* (2013.01); *A61L 2/238* (2013.01); *A61L 15/18* (2013.01); *A61L 15/46* (2013.01); *A61L 2300/104* (2013.01); *A61L 2300/404* (2013.01); *A61L 2300/606* (2013.01)

(58) Field of Classification Search
CPC .............. A61L 15/46; A61L 2300/404; A61L 2300/104; A61L 2300/606; A61L 2/08; A61L 2/238; A61L 15/18; A61K 33/38; A01N 59/16
See application file for complete search history.

(56) References Cited

U.S. PATENT DOCUMENTS

| | | | |
|---|---|---|---|
| 2,396,514 A | 3/1946 | Kreidl | |
| 2,521,713 A | 9/1950 | Goetz | |
| 2,689,809 A | 9/1954 | Fessler | |
| 2,736,721 A | 2/1956 | Dexter | |
| 2,785,106 A | 3/1957 | Mendelsohn | |
| 2,791,518 A | 5/1957 | Stokes | |
| 2,813,056 A | 11/1957 | Davis | |
| 2,934,066 A | 4/1960 | Stowasser | |
| 2,981,640 A | 4/1961 | Hill | |
| 3,092,552 A | 6/1963 | Romans | |
| 3,380,848 A | 4/1968 | Horowitz | |
| 3,385,654 A | 5/1968 | Yardney | |
| 3,685,993 A | 8/1972 | Mukherjee | |
| 3,761,590 A | 9/1973 | Fox, Jr. | |
| 3,800,792 A | 4/1974 | McKnight | |
| 3,911,115 A | 10/1975 | Hadhanyi | |
| 4,024,312 A | 5/1977 | Korpman | |
| 4,080,210 A | 3/1978 | Asada | |
| 4,226,232 A | 10/1980 | Spence | |
| 4,340,043 A | 7/1982 | Seymour | |
| 4,396,512 A | 8/1983 | Beauman | |
| 4,446,124 A | 5/1984 | Fox, Jr. | |
| 4,592,920 A | 6/1986 | Murtfeldt | |
| 4,599,226 A | 7/1986 | Fox, Jr. | |
| 4,603,152 A | 7/1986 | Laurin | |
| 4,646,730 A | 3/1987 | Schonfeld | |
| 4,652,465 A | 3/1987 | Koto | |
| 4,728,323 A | 3/1988 | Matson | |
| 4,864,042 A | 9/1989 | Armstrong | |
| 4,902,503 A | 2/1990 | Umemura | |
| 4,902,565 A | 2/1990 | Brook | |
| 4,906,466 A | 3/1990 | Edwards | |
| 5,088,978 A | 2/1992 | Hillman | |
| 5,232,748 A | 8/1993 | Horowitz | |
| 5,254,285 A | 10/1993 | Fujita | |
| 5,326,567 A | 7/1994 | Capelli | |
| 5,393,831 A | 2/1995 | Hudson | |
| 5,413,788 A | 5/1995 | Edwards | |
| 5,422,068 A * | 6/1995 | Shalaby et al. ................. 422/22 |
| 5,429,819 A | 7/1995 | Oka | |
| 5,454,886 A | 10/1995 | Burrell | |
| 5,470,585 A | 11/1995 | Gilchrist | |
| 5,512,041 A | 4/1996 | Bogart | |
| 5,516,581 A | 5/1996 | Kreckel | |
| 5,599,648 A | 2/1997 | Kondo | |
| 5,681,575 A | 10/1997 | Burrell | |
| 5,695,857 A | 12/1997 | Burrell | |

(Continued)

FOREIGN PATENT DOCUMENTS

| | | |
|---|---|---|
| CA | 2428922 | 11/2004 |
| CA | 2460585 | 11/2004 |

(Continued)

OTHER PUBLICATIONS

Emory et al. "Direct Observation of Size-Dependent Optical Enhancement in Single Metal Nanoparticles" J. Am. Chem. Soc. (1998), vol. 120, pp. 8009-8010.*

"The Carbohydrates *Chemistry and Biochemistry*"; Second Edition; Edited by W. Pigman and D. Horton; 1970; pp. 426-427.

Antelman "Silver (II, III) Disinfectants." Soap/Cosmetics/Chemical Specialties. Mar. 1994. pp. 52-59.

(Continued)

*Primary Examiner* — Abigail Fisher
*Assistant Examiner* — Daniel L Branson
(74) *Attorney, Agent, or Firm* — 3M Innovative Properties Company; Lynn R. Hunsberger

(57) ABSTRACT

A silver composition comprising silver sulfate, methods of making antimicrobial articles, particularly packaged antimicrobial articles, methods of whitening antimicrobial articles, and packaged antimicrobial articles.

23 Claims, No Drawings

(56) References Cited

U.S. PATENT DOCUMENTS

| | | |
|---|---|---|
| 5,709,870 A | 1/1998 | Yoshimura |
| 5,744,151 A | 4/1998 | Capelli |
| 5,770,255 A | 6/1998 | Burrell |
| 5,830,496 A | 11/1998 | Freeman |
| 5,848,995 A | 12/1998 | Walder |
| 5,876,489 A | 3/1999 | Kunisaki |
| 5,897,673 A | 4/1999 | Nishida |
| 5,958,440 A | 9/1999 | Burrell |
| 5,985,308 A | 11/1999 | Burrell |
| 6,017,553 A | 1/2000 | Burrell |
| 6,039,940 A | 3/2000 | Perrault |
| 6,087,549 A | 7/2000 | Flick |
| 6,126,931 A | 10/2000 | Sawan |
| 6,156,678 A | 12/2000 | Mukaida |
| 6,183,770 B1 | 2/2001 | Muchin |
| 6,194,332 B1 | 2/2001 | Rock |
| 6,201,164 B1 | 3/2001 | Wulff |
| 6,224,983 B1 | 5/2001 | Sodervall |
| 6,267,590 B1 | 7/2001 | Barry |
| 6,277,892 B1 | 8/2001 | Deckner |
| 6,288,076 B1 | 9/2001 | Kostyniak |
| 6,297,335 B1 | 10/2001 | Funk |
| 6,333,093 B1 | 12/2001 | Burrell |
| 6,355,858 B1 | 3/2002 | Gibbins |
| 6,436,420 B1 | 8/2002 | Antelman |
| 6,468,521 B1 | 10/2002 | Pedersen |
| 6,548,727 B1 | 4/2003 | Swenson |
| 6,592,888 B1 | 7/2003 | Jensen |
| 6,605,751 B1 | 8/2003 | Gibbins |
| 6,669,981 B2 | 12/2003 | Parsons |
| 6,706,260 B1 | 3/2004 | Tanaka |
| 6,716,895 B1 | 4/2004 | Terry |
| 6,797,743 B2 | 9/2004 | McDonald |
| 6,843,784 B2 | 1/2005 | Modak |
| 7,285,576 B2 | 10/2007 | Hyde |
| 7,745,509 B2 | 6/2010 | Burton |
| 8,124,826 B2 | 2/2012 | Addison |
| 2001/0010016 A1 | 7/2001 | Modak |
| 2002/0004951 A1 | 1/2002 | Auger |
| 2002/0051823 A1 | 5/2002 | Yan |
| 2002/0073891 A1 | 6/2002 | Parsons |
| 2002/0123710 A1 | 9/2002 | Worthley |
| 2003/0021832 A1 | 1/2003 | Scherr |
| 2003/0021854 A1* | 1/2003 | Burrell et al. .................. 424/618 |
| 2003/0026848 A1 | 2/2003 | Joshi |
| 2003/0032765 A1 | 2/2003 | McDonald |
| 2003/0043341 A1 | 3/2003 | Turner |
| 2003/0049300 A1 | 3/2003 | Terry |
| 2003/0054046 A1 | 3/2003 | Burrell |
| 2003/0108608 A1 | 6/2003 | Laridon |
| 2003/0113378 A1 | 6/2003 | Laridon |
| 2003/0118624 A1 | 6/2003 | Jackson |
| 2003/0118733 A1 | 6/2003 | Jackson |
| 2003/0180346 A1 | 9/2003 | Woods |
| 2003/0185889 A1 | 10/2003 | Yan |
| 2003/0190851 A1 | 10/2003 | Yan |
| 2004/0126433 A1 | 7/2004 | Parsons |
| 2004/0180093 A1 | 9/2004 | Burton |
| 2004/0214809 A1 | 10/2004 | Capelli |
| 2004/0229034 A1 | 11/2004 | Djokic |
| 2005/0079200 A1 | 4/2005 | Rathenow et al. |
| 2005/0123590 A1 | 6/2005 | Burton |
| 2005/0123621 A1 | 6/2005 | Burton |
| 2005/0124724 A1 | 6/2005 | Burton |
| 2006/0034899 A1 | 2/2006 | Ylitalo |
| 2006/0035039 A1 | 2/2006 | Ylitalo |
| 2006/0141015 A1 | 6/2006 | Tessier |
| 2006/0173087 A1 | 8/2006 | Hyde |
| 2006/0233888 A1 | 10/2006 | Burton |
| 2006/0233889 A1 | 10/2006 | Burton |
| 2007/0166399 A1 | 7/2007 | Burton |
| 2010/0098949 A1 | 4/2010 | Burton |
| 2010/0233273 A1 | 9/2010 | Burton |

FOREIGN PATENT DOCUMENTS

| | | |
|---|---|---|
| CN | 1123665 | 6/1996 |
| CN | 1128188 | 8/1996 |
| CN | 1291667 | 4/2001 |
| CN | 1308102 | 8/2001 |
| CN | 1317033 | 10/2001 |
| CN | 1322874 | 11/2001 |
| CN | 1328819 | 1/2002 |
| CN | 1348032 | 5/2002 |
| CN | 1369206 | 9/2002 |
| CN | 1379146 | 11/2002 |
| CN | 1214867 | 1/2004 |
| CN | 1241662 | 8/2004 |
| CN | 1605676 | 4/2005 |
| DE | 2260536 | 7/1974 |
| DE | 273846 | 11/1989 |
| DE | 4226810 | 1/1994 |
| DE | 19958697 | 6/2001 |
| DE | 10023336 | 9/2001 |
| EP | 0255248 | 2/1988 |
| EP | 0272149 | 6/1988 |
| EP | 0512855 | 5/1991 |
| EP | 0984698 | 4/2003 |
| GB | 591440 | 8/1947 |
| GB | 769799 | 3/1957 |
| GB | 2127389 | 4/1984 |
| GB | 2134791 | 8/1984 |
| GB | 2272641 | 5/1994 |
| JP | 54-074841 | 6/1979 |
| JP | 54152696 | 12/1979 |
| JP | 63012723 | 2/1988 |
| JP | 1274807 | 11/1989 |
| JP | 2004376 | 1/1990 |
| JP | 02303818 | 12/1990 |
| JP | 3193047 | 8/1991 |
| JP | 04007004 | 1/1992 |
| JP | 04163137 | 6/1992 |
| JP | 4272754 | 9/1992 |
| JP | 4272764 | 9/1992 |
| JP | 4272765 | 9/1992 |
| JP | 517617 | 1/1993 |
| JP | 05-059662 | 3/1993 |
| JP | 557002 | 3/1993 |
| JP | 06-313266 | 11/1994 |
| JP | 07149943 | 6/1995 |
| JP | 7-258972 | 10/1995 |
| JP | 08-029944 | 2/1996 |
| JP | H09505112 | 5/1997 |
| JP | 10165809 | 6/1998 |
| JP | 11-507679 | 7/1999 |
| JP | 2002233708 | 8/2002 |
| JP | 2005002033 | 1/2005 |
| JP | 2007511313 | 5/2007 |
| WO | WO 8401721 | 5/1984 |
| WO | WO 8902754 | 4/1989 |
| WO | WO 92/18098 | 10/1992 |
| WO | WO 9312275 | 6/1993 |
| WO | WO 95/13704 | 5/1995 |
| WO | WO 9601119 | 1/1996 |
| WO | WO 96/39464 | 12/1996 |
| WO | WO 9700163 | 1/1997 |
| WO | WO 9702038 | 1/1997 |
| WO | WO 98/28013 | 7/1998 |
| WO | WO 9841095 | 9/1998 |
| WO | WO 9915101 | 4/1999 |
| WO | WO 0001424 | 1/2000 |
| WO | WO 0009173 | 2/2000 |
| WO | WO 0049219 | 8/2000 |
| WO | WO 0071183 | 11/2000 |
| WO | WO 01/24839 A1 * | 4/2001 |
| WO | WO 0124839 | 4/2001 |
| WO | WO 0143549 | 6/2001 |
| WO | WO 0143788 | 6/2001 |
| WO | WO 0218003 | 3/2002 |
| WO | WO 0218699 | 3/2002 |
| WO | WO 0224240 | 3/2002 |
| WO | WO 02/47737 | 6/2002 |
| WO | WO 0243743 | 6/2002 |

(56) References Cited

FOREIGN PATENT DOCUMENTS

| WO | WO 02062403 | 8/2002 |
|---|---|---|
| WO | WO 02078755 | 10/2002 |
| WO | WO 02090025 | 11/2002 |
| WO | WO 03022317 | 3/2003 |
| WO | WO 03046273 | 6/2003 |
| WO | WO 03047636 | 6/2003 |
| WO | WO 03/060008 | 7/2003 |
| WO | WO 03053484 | 7/2003 |
| WO | WO 03080911 | 10/2003 |
| WO | WO 2004017738 | 3/2004 |
| WO | WO 2004080499 | 9/2004 |
| WO | WO 2004101014 | 11/2004 |
| WO | WO 2004112850 | 12/2004 |
| WO | WO 2005038122 | 4/2005 |
| WO | WO 2005/056067 | 6/2005 |
| WO | WO 2005056070 | 6/2005 |
| WO | WO 2006113052 | 10/2006 |
| WO | WO 2008/060795 | 5/2008 |

OTHER PUBLICATIONS

ASTM D2244-05, "Standard Practice for Calculation of Color Tolerances and Color Differences from Instrumentally measured Color Coordinates," *Annual Book of ASTM Standards*, Oct. 1, 2005, pp. 239-248.

ASTM D3985-02, "Standard Test Method for Oxygen Gas Transmission Rate Through Plastic Film and Sheeting Using a Coulometric Sensor," *Annual Book of ASTM Standards*, May 10, 2002, pp. 460-465.

Brochure entitled "Ciba® SALCARE® SC95—Rheology Modifier" from Ciba Specialty Chemcials 2001 (5 pgs.).

Calvert et al.; "Photochemistry"; Chapter II; John Wiley & Sons Inc. (1966) pp. 27-125.

D. Acel; "Uber die oligodynamische Wirkung der Metalle."; Biochemische Zeitschrift; pp. 23-26; Aug. 21, 1920.

Dean, John A., "Section 3.2," *Lange's Handbook of Chemistry*, McGraw-Inc., Fifteenth Edition, 1998, pp. 3.11, 3.64 and 3.65.

Feng et al; "A mechanistic study of the antibacterial effect of silver ions on *Escherichia coli* and *Staphylococus aureus*"; J. Biomed Mater Res 15 (52); (pp. 662-668 (2000).

Furr et al. "Antibacterial Activity of Actisorb Plus, Actisorb and Silver Nitrate." 1994 J. Hosp. Infect. 27:201-208.

Gibbins et al.; Clinical study entitled "An In-Vitro Comparison of a New Antimicrobial Polyacrylate Absorbent Wound Dressing Containing Silver with the Silver-Containing Antimicrobial Film Dressings" from AcryMed dated Oct. 1999 (7 pgs.) printed Sep. 27, 2001.

J. Gibbarb, "Public Health Aspects of the Treatment of Water and Beverages With Silver"; American Journal of Public Health; Feb. 1937; vol. 27, pp. 112-119.

J. He et al.; "Facile In Situ Synthesis of Noble Metal Nanoparticles in Porous Cellulose Fibers"; Chem. Mater. 2003, vol. 15, No. 23, pp. 4401-4406.

Lansdown, A.; "Silver 1: its antibacterial properties and mechanism of action"; Journal of Wound Care; vol. 11; No. 4, Apr. 2002; pp. 125-130.

Lansdown, A.; "Silver 2: toxicity in mammals and how its products aid wound repair"; Journal of Wound Care; vol. 11, No. 5, May 2002; pp. 173-177.

M. Fetizon et al.; "Chimie Organique"; Comptes Rendus; Series C, 275; Sep. 18, 1972; pp. 621-623.

N. Grier; "Silver and Its Compound"; Disinfection, Sterilization and Preservation ($3^{rd}$ Ed.) Ch. 18, pp. 375-389.

Nomiya et al. "Syntheses, Crystal Structures and Antimicrobial Activities of Polymeric Silver(1) Complexes with Three Amin-Acids [aspartic acid (H2asp), Glycine (Hgly) and Asparagine (Hasn)]" 2002 J. Chem. Soc. Dalton Trns. pp. 2483-2490.

Odian, G.; "Principles of Polymerization"; $3^{rd}$ Edition; 1991; 16 pgs. Table of Contents and pp. 352-353.

Russell et al.; "Antimicrobial Activity and Action of Silver"; Progress in Medicinal Chemistry; vol. 31; 1994; pp. 351-370.

Sheet entitled "Rheology Modifiers" from Ciba Specialty Chemicals 2001 (1 pg.).

Thomas et al. "A Comparison of Antimicrobial Effects of Four Silver-Containing Dressings on Three Organisms." 2003 J. Wound Care 12(3):101-107.

Tredget et al. "A Match-Pair, Randomized Study Evaluating the Efficacy and Safety of Acticoat* Silver-Coated Dressings for the Treatment of Burn Wounds." 1998 J. Burn Care and Rehab. 19(6):531-537.

Wright et al. "Wound Management in an Era of Increasing Bacterial Antibiotic Resistance: A Role for Topical Silver Treatment." 1998 AJIC 26(6):572-577.

Wright et al.; "The Comparative Efficacy of Two Antimicrobial Barrier Dressings": In vitro Examination of Two Controlled Release of Silver Dressings; Wounds 10(6); pp. 179-188, 1998 © Health Management Publications, Inc.

Yuranova et al., Antibacterial textiles prepared by RF-plasma and vacuum-UV mediated deposition of silver, Journal of Photochemistry and photo biology A: Chemistry, vol. 161, Issue 1, Nov. 17, 2003, pp. 27-34, ISSN 1010-6030, 10.1016/S1010-6030(03)00204-1.

PCT International Search Report for PCT/US2007/000594 mailed Jun. 25, 2007.

U.S. Appl. No. 11/550,434, filed Oct. 18, 2002; and entitled "Antimicrobial Articles and Methods of Manufacture."

"Sterility Assurance Compliance—A guide for medical device manufactures" *SGS Life Science Services*, Rev. 1.1, May 2007, 34 pgs. Available online at <http://www.us.sgs.com/sterility_assurance_2007.pdf>, retrieved on Oct. 22, 2009.

ASTM D 2369-03 "Standard Test Method for Volatile Content of Coatings," *Annual Book of ASTM Standards*, vol. 15.05; 2003: p. 277-280.

ASTM D3759-83 "Standard Test Method for Tensile Strength and Elongation of Pressure-Sensitive Tapes," *Annual Book of ASTM Standards*, vol. 14.02; 1983: p. 662-670.

ASTM F1249-01 "Standard Test Method for Water Vapor Transmission Rate through Plastic Film and Sheeting Using a Modulated Infared Sensor," *Annual Book of ASTM Standards*, vol. 11.03; 2001: p. 1289-1293.

Handbook of Chemistry, Norbert Adolph Lange, Ph.D., Handbook Publisher's Inc., $2^{nd}$ Edition, 1937.

Lange's Handbook of Chemistry, John A. Dean, McGraw-Hill, Inc., $14^{th}$ Edition, 1992.

Nesbitt et al., "Solubility Studies of Silver Sulfadiazine," *Journal of Pharmaceutical Sciences*, Apr. 1977;66(4):519-522.

\* cited by examiner

SILVER-CONTAINING ANTIMICROBIAL ARTICLES AND METHODS OF MANUFACTURE

CROSS REFERENCE TO RELATED APPLICATIONS

This application is a divisional application of U.S. patent application Ser. No. 12/160,439, filed Jul. 10, 2008 now U.S. Pat. No. 8,192,764, which is a national stage filing under 35 U.S.C. 371 of PCT/US2007/000594, filed Jan. 10, 2007, which claims priority to U.S. Ser. No. 11/331,867, filed Jan. 13, 2006, the disclosures of which is incorporated by reference in their entirety herein.

BACKGROUND

While wounds heal more effectively in moist environments, bacterial infection poses increased risk. Use of antibiotics to treat bacterial infections can build bacterial resistance. Silver compounds are known to impart antimicrobial effects to a surface with minimal risk of developing bacterial resistance. Silver is delivered to the surface by sustained release of silver ions from the surface when in contact with moist environments, such as a wound bed.

Silver compositions, such as silver nitrate and silver sulfadiazine, are effective antimicrobials used in a variety of applications. However, they are typically not light stable, leave a stain on skin with which they come into contact, and in the case of silver nitrate, can be quickly depleted in an aqueous environment. Use of silver salts as antimicrobials have included the use of stabilizing agents to increase light stability such as those described in U.S. Pat. No. 2,791,518 (Stokes et al.) (using a first solution of ammonia, silver nitrate and barium nitrate; and a second solution of sodium chloride and sodium sulfate); and in U.S. Pat. No. 6,669,981 (Parsons et al.) (a silver salt in water/organic solvent followed by one or more stabilizing agents (e.g., ammonium salts, thiosulphates, chlorides and/or peroxides)).

SUMMARY

The present invention is directed to methods of making antimicrobial articles, particularly packaged antimicrobial articles, methods of whitening antimicrobial articles, and packaged antimicrobial articles.

In one embodiment, the present invention provides a method of making a packaged antimicrobial article. The method includes: preparing a composition comprising silver sulfate; coating the silver sulfate composition on a substrate; drying the coated substrate to form an antimicrobial article; placing the antimicrobial article in packaging material having a volatile organic content of no greater than 100 mg per square meter; and sealing the packaging material with the antimicrobial article therein.

In another embodiment, the present invention provides a method of whitening at least a portion of an antimicrobial article. The method includes: providing a packaged antimicrobial article having at least a portion colored other than white, wherein the article includes a substrate coated with a silver salt composition including at least a portion of the silver in the zero-valent state, and wherein the antimicrobial article is sealed within packaging material having a volatile organic content of greater than 100 milligrams per square meter (100 mg/m$^2$); and irradiating the packaged antimicrobial article to whiten at least a portion of the antimicrobial article.

In other embodiments, the present invention provides packaged antimicrobial articles. In one embodiment, a packaged antimicrobial article includes: an antimicrobial article including a substrate coated with a silver sulfate composition; and packaging having the antimicrobial article sealed therein; wherein the packaging comprises material having a volatile organic content of no greater than 100 mg/m$^2$.

In certain preferred embodiments of the present invention, antimicrobial articles are color stable, particularly during and/or after irradiation. In this context, "color stable" means that the color of the dried silver sulfate composition coated on a substrate does not exhibit a significant change in color and/or color homogeneity to the human eye over time (preferably at least 4 hours, more preferably at least 8 hours, even more preferably at least 48 hours, and even more preferably at least 1 week) when compared to the same coated composition on a substrate that has not been exposed to light (e.g., fluorescent, natural, UV). Preferably, "color stable" means that the color of the dried silver sulfate composition coated on a substrate does not exhibit a perceptible change to the human eye over time (preferably at least 4 hours, more preferably at least 8 hours, even more preferably at least 48 hours, and even more preferably at least 1 week) when compared to the same coated composition on a substrate that has not been exposed to light (e.g., fluorescent, natural, UV).

Color change can be evaluated in a number of ways using a number of grading scales. For example, color change can be evaluated by visual ranking under fluorescent lighting. Samples are compared to color standards and given a rating based on that visual comparison. In this ranking scale, 0, 1, and 2 are classified as "whitish" including white to cream, 3 through 5 are classified as "yellowish" including light yellow to golden yellow, and 6 through 10 are classified as rust to dark brown. Color change is the difference in ratings obtained by subtracting the initial rating from the rating after treatment. Positive ratings represent a darkening in appearance and negative ratings represent a lightening in appearance. A color change on this scale of 1 or less is acceptable as long as the color is substantially homogeneous. If the color is non-homogeneous, even a color change of 0.5 is considered a "significant" and unacceptable change.

Color change can also be measured using a colorimeter such as a Minolta Chroma Meter (CR-300, manufactured by Konica Minolta Photo Imaging U.S.A., Inc., Mahwah, N.J.) using tristimulus values. A color change on this scale in the "Y" value of 15% or less is acceptable as long as the color is homogeneous. If the color is non-homogeneous, even a color change of 5% in the "Y" value is considered a "significant" and unacceptable change.

Color change can also be measured using a colorimeter according to ASTM D2244. The resulting CIELAB color difference (DE*), between the sample after exposure for the indicated period of time and the unexposed sample can be determined. For purposes of reference only, a DE*, or color change of about 2 units is just detectable by the naked eye whereas a DE* of 20 or greater represents a substantial or "significant" and unacceptable color change.

In certain preferred embodiments of the present invention, antimicrobial articles are maintained in an environment of no more than 50% RH (i.e., a water activity of 0.5) at room temperature. In certain preferred embodiments of the present invention, antimicrobial articles are maintained in an environment of no more than 30% RH at room temperature. In this context "room temperature" means an average room temperature, typically 23° C.+/−2° C. "Relative humidity" the ratio of the quantity of water vapor present in the atmosphere to the quantity that would saturate the atmosphere at the given temperature.

As used herein, "a," "an," "the," "at least one," and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The above summary of the present invention is not intended to describe each disclosed embodiment or every implementation of the present invention. The description that follows more particularly exemplifies illustrative embodiments.

DETAILED DESCRIPTION OF ILLUSTRATIVE EMBODIMENTS OF THE INVENTION

The present invention is directed to methods of making antimicrobial articles, particularly packaged antimicrobial articles, methods of whitening antimicrobial articles, and packaged antimicrobial articles.

In certain embodiments, the antimicrobial articles are prepared using a composition including silver sulfate (e.g., an aqueous-based composition), coating the silver sulfate composition on a substrate, and drying the coated substrate to form an antimicrobial article. The antimicrobial article is placed in packaging material and the packaging material sealed with the antimicrobial article therein. Accordingly, the present invention provides a packaged antimicrobial article that includes an antimicrobial article that includes a substrate coated with a silver sulfate composition, and packaging having the antimicrobial article sealed therein. In certain embodiments, the antimicrobial article sealed in the packaging material is irradiated.

In certain embodiments, the packaging includes material having a volatile organic content of no greater than 100 milligrams per square meter ($mg/m^2$). In other embodiments, the volatile organic content is no greater than 50 mg per square meter. In this context, the "volatile organic content" is defined by the equation: (mass of packaging material before oven exposure—mass of packaging material after oven exposure)/surface area. This can be determined using ASTM D 2369-03 as described in the Examples Section.

Useful packaging materials for the present invention may be porous or nonporous, as long as it maintains sterility of the product after sterilization. Useful packages may include one or more layers of materials. There may be one or more packages surrounding a substrate. For example, there may be one or more inner pouches within an outer pouch. In such a situation, the innermost pouch (i.e., the one in direct contact with the antimicrobial article) is preferably porous. Sufficient porosity can allow for transfer of gases released during irradiation of the packaged antimicrobial article. Typically, in such a situation where the innermost pouch is porous, the outermost pouch of the packaging material is nonporous or of very low porosity, particularly with respect to oxygen permeability and moisture vapor permeability.

In certain embodiments, the packaging includes material having an oxygen permeability of less than 0.01 cubic centimeter per 645 square centimeters per 24 hours. In this context, "oxygen permeability" is defined as the volume of oxygen gas that diffuses through 645 square centimeters (100 square inches) of packaging film during 24 hours. This can be determined using ASTM D3985.

In certain embodiments, the packaging includes material having a moisture vapor transmission rate (MVTR) of less than 0.01 gram per 645 square centimeters per 24 hours. In this context, the MVTR is the mass of water that diffuses through 645 square centimeters (100 square inches) of packaging film during 24 hours. This can be determined using ASTM F1249.

Packaging materials having such properties include TPC-0765B/TPC-0760B construction (Tolas Health Care; Feasterville, Pa.) and Techni-Pouch package (Technipaq, Inc., Crystal Lake, Ill.) with a PET (polyester)/Aluminum Foil/LLDPE (linear low density polyethylene) material construction.

In certain embodiments, the packaging includes a porous material having a Gurley Hill porosity of less than 100 seconds per 100 cubic centimeters of air (100 s/100 cc air). In certain embodiments, the porosity is at least 5 seconds per 100 cubic centimeters of air. Porous packaging materials having this property include those commercially available under the tradename TYVEK such as TYVEK 1073B/TPF-0501A (a TYVEK/film construction) available from Tolas Health Care Packaging, Feasterville, Pa.; and paper/film type packaging construction such as that available under the tradename CONVERTERS Sterilization Pouches (e.g., 3 inch×8 inch (7.5 cm×20 cm) size; Catalog 90308) distributed by Cardinal Health of McGaw Park, Ill.

In certain embodiments, the packaging material includes an inner pouch and an outer pouch, wherein the inner pouch has a Gurley Hill porosity of less than 100 s/100 cc of air (preferably of 5 s to 100 s/100 cc of air), and the outer pouch has an oxygen permeability of less than 0.01 cubic centimeter per 645 square centimeters per 24 hours and/or a moisture vapor transmission rate of less than 0.01 gram per 645 square centimeters per 24 hours.

In certain embodiments, an antimicrobial article is made by dissolving silver sulfate in an aqueous-based composition, coating the composition on a substrate, and drying the coated substrate. In certain embodiments, the substrate coated with silver sulfate remains stable to light (e.g., visible, UV) and heat without the addition of traditional stabilizing agents such as ammonia, ammonium salts (e.g., ammonium acetate, ammonium sulfate, and ammonium carbonate), thiosulfates, water insoluble salts of metals (e.g., halides such as chlorides), peroxides, magnesium trisilicate, and/or polymers. Preferably, any component that would function as a stabilizing agent is present in amounts less than 100 parts per million (ppm), more preferably less than 50 ppm, most preferably less than 20 ppm, based on the total weight of the silver sulfate composition. Alternatively, any component that would function as a stabilizing agent is present in amounts less than 1000 ppm, more preferably less than 500 ppm, most preferably less than 100 ppm, based on the total weight of the antimicrobial article comprising a dried silver sulfate composition coated on a substrate.

The resultant solution containing the silver sulfate solution can be coated on a substrate, preferably an absorbent substrate, although nonabsorbent substrates can also be used. The coated substrate is dried to drive off the volatile components, such as water and organic solvents (e.g., methanol, ethanol, isopropanol, acetone, or other organic solvents that are miscible with water). Drying can be accomplished at room temperature or by heating the coated substrate. Heat will speed the drying process. In a preferred embodiment, the coated substrate is dried at temperatures below 190° C., more preferably below 170° C., even more preferably below 140° C., to minimize reduction of the silver compounds, and also prevent the oxidation of a cellulosic material, when used as a substrate.

Further, tensile strength of an oxidizable substrate (such as cotton) is maximized when the silver sulfate composition on the substrate is dried at a low temperature, preferably less that 140° C., more preferable at less than 100° C., and most preferably at less than 70° C.

Once dried, the substrate remains coated with the silver sulfate. The coated composition typically contains silver sulfate in a major amount. Low levels of silver metal (i.e., zerovalent silver) may be present in amounts, preferably less than 20 wt %, and more preferably, less than 10 wt %, based on the total weight of the silver components in the composition. In some embodiments, the choice of starting materials and drying temperatures results in a coating that leaves no residue with essentially only the silver sulfate remaining on the substrate, and all other components of the silver solution removed from the substrate upon drying.

When applied, the silver sulfate solution penetrates and impregnates the interior of the substrate. For example, when gauze is used, the silver solution impregnates between the fibers of the gauze.

The concentration of silver sulfate on the substrate is a function of the amount of silver sulfate in solution, the total amount of solution applied onto a unit area of the substrate, and the drying temperature. The silver sulfate concentration on the substrate is typically less than 30 mg/cm$^2$, and in certain embodiments less than 5 mg/cm$^2$. In a preferred embodiment, the silver sulfate concentration on the substrate ranges from 0.001 mg/cm$^2$ to 5 mg/cm$^2$, and in certain embodiments from 0.001 mg/cm$^2$ to 1 mg/cm$^2$.

The substrate can be a woven or nonwoven material (e.g., a gauze) made of natural or synthetic compounds. The substrate can be a porous or nonporous film. It can be a knitted fabric, a foam, or a hydrocolloid, for example.

In certain embodiments, the substrate is a silver nitrate oxidizable substrate. In certain embodiments, the substrate includes a cellulosic material. Examples of cellulosic materials include polysaccharides or modified polysaccharides, regenerated cellulose (such as rayon), paper, cotton, those materials available under the tradename TENCEL, carboxymethyl cellulose, and the like.

Other materials may be used, including for example, polyvinylpyrrolidone, polyvinyl alcohol, polyvinyl ether, polyacrylate, polyacrylamide, collagen, gelatin, may be used. Non-absorbent substrates may also be used including, but not limited to, nylon, polyester, polyethylene, and polypropylene.

Other suitable materials for the substrate include polyacrylonitrile, polyvinylidene difluoride, polytetrafluoroethylene, polyoxymethylene, polyvinyl chloride, polycarbonate, styrene-ethylenebutylene-styrene elastomer, styrene-butylene-styrene elastomer, styrene-isoprene-styrene elastomer, and combinations thereof. Other substrate materials are disclosed herein below. Various combinations of materials may be included within the substrate. In certain embodiments, the substrate includes a material selected from the group consisting of a cellulosic material, nylon, polyester fiber, and combinations thereof. In certain embodiments, the substrate includes a cellulosic material. In certain embodiments, the cellulosic substrate includes cotton.

The method provides a silver sulfate solution for coating on a substrate without using an acid. The presence of acid can hydrolyze the cellulosic material. This aspect of the process allows the coating to be applied without weakening the cellulosic substrate. Preferably the coating solution has a pH of at least 4, more preferably at least 5. Preferably, the coating solution has a pH of no greater than 9.

Elevated temperatures can also accelerate the oxidation of cellulose by a silver salt, resulting in such affects as lowering the tensile strength and changing the color of the silver sulfate composition on the substrate. The color change on a cellulosic material, such as cotton, is likely due to the reduction of silver salt to silver metal with an accompanying oxidation of the cellulose substrate. The oxidized cotton has lower tensile strength.

If silver sulfate is coated on a cellulosic substrate or other easily oxidizable substrate (e.g., a silver nitrate oxidizable substrate), the article will change color in proportion to the drying temperature and the time in the drying device, such as an oven. Generally, no color change is observed when the substrate coated with the silver sulfate composition is dried below approximately 100° C. for 15 minutes. For example, when wetted cotton is dried at an oven temperature greater than approximately 100° C., the cotton substrate darkens in proportion to the oven temperature and turns yellow then brown then dark brown.

If a synthetic substrate such as polyester, which is not easily oxidized, is coated with silver sulfate coating solution and dried, the polyester will remain white even when dried at temperature above 100° C. Similarly, when polyester or other substrate material such as polyester, nylon, polyethylene, polypropylene, polyvinylidene difluoride, polytetrafluoroethylene, polyoxymethylene, polyvinyl chloride, polycarbonate, styrene-ethylenebutylene-styrene elastomer, styrene-butylene-styrene elastomer, or styrene-isoprene-styrene elastomer, is irradiated after being coated with silver sulfate coating solution and dried, the material does not typically change color.

The silver compositions, once coated, are preferably color stable (i.e., stable to light as defined herein). In addition, preferably the compositions are also stable to at least one of the following: heat and/or moisture. Regardless of substrate choice, preferably the coated silver sulfate composition is color stable. The initial color that the silver sulfate solution develops after drying at a particular temperature will remain without appreciable change over time (e.g., preferably at least 4 hours, more preferably at least 8 hours, even more preferably at least 48 hours, and even more preferably at least 1 week) either with or without exposure to light.

In certain situations, however, coated silver sulfate will change color. For example, in certain situations, irradiating an antimicrobial article after the article is placed in packaging and the packaging material is sealed will cause a color change. This often occurs when the substrate of the antimicrobial article includes a cellulosic material. The radiation typically includes gamma radiation and/or electron beam radiation. Such radiation is typically used to sterilize the antimicrobial articles. Thus, typical radiation levels include that which is necessary to assure a Sterility Assurance Level of $10^{-6}$, based on the AAMI Method of Sterility Assurance.

It has been discovered that this color change upon irradiation can occur in certain situations in standard packaging with a relatively high volatile organic content (i.e., one with a volatile organic content (VOC) of greater than 100 mg/m$^2$). Examples of such standard packaging include that available from Phoenix Healthcare Products, LLC, Milwaukee, Wis., and VP Group, Feuchtwangen, Germany. The use of packaging material having a volatile organic content of no greater than 100 mg/m² as described herein, however, in certain situations will reduce, and often eliminate, such a radiation-induced color change.

Low VOC packaging can be particularly useful when the color of the article is changed from the initial color (e.g., whitish) to a yellowish color, or some color other than a whitish color. Heat can cause a color change to a state that is more stable to irradiation than the initial color. For example, a silver sulfate composition that is dried to a whitish state will darken when irradiated in packaging regardless of the volatile organic content; however, when it is heated to a temperature that causes the color to change to yellowish, this state is generally more stable to irradiation and will typically not change color when irradiated in a low VOC package (i.e., one with no greater than 100 gm/m² VOC), particularly when low humidity conditions are used to package the article, although it will in a high VOC package (unless large amounts of substrate material are used relative to the amount of packaging material). For certain embodiments, the present invention provides a method of making a packaged antimicrobial article that includes drying the coated substrate at a temperature that causes the silver sulfate composition to develop a yellowish color (typically due to the formation of silver in the zero valence state during drying), which is color stable during and/or after irradiation (typically, after irradiation, and preferably during and after irradiation). This is particularly true for yellowish articles in low VOC packaging (i.e., no greater than 100 gm/m² VOC) during and after e-beam irradiation, or with yellowish articles in low VOC packaging after gamma irradiation (although there may be a color change during gamma irradiation), or with yellowish articles in low VOC packaging during and after gamma irradiation when low humidity packaging conditions are used (e.g., 30% RH or lower).

Whitish articles are not necessarily as color stable as yellowish articles under similar conditions; however, whitish articles can be color stable in low VOC packaging with activated carbon in the packaging, particularly after e-beam or gamma irradiation. Thus, the present invention provides a method of making a packaged antimicrobial article that includes: preparing a composition including silver sulfate; coating the silver sulfate composition on a substrate; drying the coated substrate occurs at a temperature that causes the silver sulfate composition to develop a whitish color; placing the antimicrobial article in packaging material having a volatile organic content of no greater than 100 mg per square meter; and sealing the packaging material with the antimicrobial article therein; wherein activated carbon is present in the packaging, and further wherein the antimicrobial article is color stable during and after irradiation.

Low VOC packaging, however, is not necessarily required with a yellowish article when the amount of substrate of the article is greater than 2 mg per interior square centimeter of packaging material. Thus, the present invention provides a color stable packaged antimicrobial article (and a method of making) that includes: an antimicrobial article including a substrate coated with a silver sulfate composition; and packaging having the antimicrobial article sealed therein; wherein the packaging includes material having a volatile organic content of greater than 100 mg per square meter; and wherein the ratio of antimicrobial article substrate to packaging material is greater than 2 mg substrate per interior square centimeter packaging material. The dried coated substrate includes silver in the zero-valent state, has a yellowish color, and preferably is color stable after irradiation.

The color stability of the coated silver sulfate composition provides several advantages. The color stability provides an indication to the end user that the product is of consistent high quality. Further, the color stability indicates that the form of silver on the substrate has not appreciably changed which indicates that its performance (i.e., silver release, antimicrobial activity) is essentially constant over time in the package (e.g., preferably, at least 1 month, more preferably at least 2 months, even more preferably at least 6 months, and even more preferably at least 1 year). Thus, the use of packaging as described herein is desirable when antimicrobial articles of the present invention are irradiated and such color stability is desirable.

Such compositions are useful in medical articles, particularly wound dressings and wound packing materials, although a wide variety of other products can be coated with the silver sulfate compositions.

Stability of the silver sulfate coated substrate is prolonged and/or increased when the relative humidity (RH) at room temperature (particularly during the packaging process) is maintained at 50% or lower; more preferably at 30% or lower; and most preferably at 20% or lower. Relative humidity can be reduced to 30%, and preferably to 20%, or lower, for the silver sulfate coated substrate by a number of methods including: 1) placing the coated substrate in an environment that has a relative humidity of 30% or lower, and preferably 20% or lower, and then packaging the product in the same environment; 2) drying the mesh in an oven, then immediately packaging the mesh; and 3) addition of a desiccant within the package. Preferably, to maintain a low relative humidity in the dried silver sulfate composition, the article should be packaged in a package with a low moisture vapor transmission rate (MVTR) such as a Techni-Pouch package (Technipaq, Inc., Crystal Lake, Ill.) with a PET/Aluminum Foil/LLDPE material construction. Low relative humidity increases the thermal stability of silver sulfate treated cotton.

In certain situations, it may be desirable to take advantage of the color change irradiation (e.g., gamma radiation and/or electron beam radiation) can cause in packaging with a volatile organic content of greater than 100 mg/m². Thus, the present invention also provides a method of whitening at least a portion of an antimicrobial article. For example, if an antimicrobial article has at least a portion colored other than whitish, wherein the article includes a substrate coated with a silver salt composition including at least a portion of the silver in the zero-valent state, irradiating can whiten the colored portion.

Silver compounds, including silver sulfate, provide sustained release of silver ions over time based in part on their limited solubility and inherent dissociation equilibrium constants. The silver sulfate composition may have other silver salts, including those that are not color stable, in varying amounts, as long as the composition when coated on the substrate remains color stable. In addition to silver sulfate, other silver compounds that may be coated on a substrate in addition to the silver sulfate include silver oxide, silver acetate, silver nitrate, silver citrate, silver chloride, silver lactate, silver phosphate, silver stearate, silver thiocyanate, silver carbonate, silver saccharinate, silver anthranilate, silver benzoate, and combinations thereof. Silver metal may also be present on the substrate. Preferably, the amount of silver compounds other than silver sulfate is less than 20 wt %, more preferably less than 10 wt %, based on the total weight percentage (wt %) of the silver components in the silver sulfate composition coated on the substrate.

The silver sulfate coated substrate remains stable when it contains silver sulfate in combination with other silver salts with limited color stability. Preferably, the amount of silver sulfate is at least 60 wt %, more preferably at least 75 wt %, and most preferably at least 90 wt %, based on the total weight percentage (wt %) of the silver components in the silver sulfate composition coated on the substrate.

Articles can be prepared using the silver solution described herein according to a variety of coating methods. When a porous substrate is coated, the process used typically allows the yarns, filaments, or film such as perforated or microporous film, to be coated, while leaving most of the apertures unobstructed by the composition. Depending on the structure of the support used, the amount of solution employed will vary over a wide range.

The silver sulfate coating solution can be prepared by mixing silver sulfate and distilled water. The silver sulfate coating solution can have a range of concentrations up to a water solubility of about 0.6% at room temperature. Optionally, higher concentrations of silver sulfate can be obtained by dissolving silver sulfate in hot water. Optionally sulfate in other forms may be added, such as sodium sulfate.

The process can be accomplished as a continuous process, or it can be done in a single step or with a single coating solution. The process to apply the coating does not require elevated temperatures, and can be applied at temperatures less than 70° C. The coating solution can be maintained below a pH of 9, and preferably less than 7, to minimize adverse effects to the substrate. The coating solution can be maintained at a pH above 4.

According to a variant of this process, a substrate can be passed through a bath of the silver composition. The substrate covered with the silver sulfate composition is then dried, for example in an oven at a temperature sufficient to evaporate constituents of the solution. The temperature is preferably less than 190° C., more preferably less than 170° C., and most preferably less than 140° C.

The silver sulfate solution can also be coated onto a carrier web or a backing (described below) using a known coating technique such as gravure coating, curtain coating, die coating, knife coating, roll coating, or spray coating. A preferred coating method is gravure coating.

Medical Articles

The silver compositions of the present invention can be used in a wide variety of products, although they are preferably used in medical articles. Such medical articles can be in the form of a wound dressing, wound packing material, or other material that is applied directly to or contacts a wound. Other potential products include clothing, bedding, masks, dust cloths, shoe inserts, diapers, and hospital materials such as blankets, surgical drapes and gowns.

The silver compositions can be coated on various backings (i.e., a support substrate). The backing or support substrate can be porous or nonporous. The composition of the present invention can be coated on the support substrate or impregnated into it, for example.

Suitable materials are preferably flexible, and may be fabric, non-woven or woven polymeric webs, polymer films, hydrocolloids, foam, metallic foils, paper, and/or combinations thereof. More specifically, cotton gauze is useful with the silver compositions of the present invention. For certain embodiments it is desirable to use a permeable (e.g., with respect to moisture vapor), open apertured substrate (i.e., a scrim). For certain embodiments, the substrate may be a hydrocolloid, such as a hydrophilic polymer, or hydrophobic polymer matrix containing hydrophilic particles, as described in U.S. Pat. App. Pub. Nos. 2004/0180093 and 2005/0124724.

The substrates (i.e., backings) are preferably porous to allow the passage of wound fluids, moisture vapor, and air. In certain embodiments, the substrates are substantially impervious to liquid, especially wound exudate. In certain embodiments, the substrates are capable of absorbing liquid, especially wound exudate. In certain embodiments, the substrate is an apertured liquid permeable substrate.

Suitable porous substrates include knits, wovens (e.g., cheese cloth and gauze), nonwovens (including spun-bonded nonwovens, and BMF (blown micro fibers), extruded porous sheets, and perforated sheets. The apertures (i.e., openings) in the porous substrates are of sufficient size and sufficient number to facilitate high breathability. For certain embodiments, the porous substrates have at least 1 aperture per square centimeter. For certain embodiments, the porous substrates have no greater than 225 apertures per square centimeter. For certain embodiments, the apertures have an average opening size (i.e., the largest dimension of the opening) of at least 0.1 millimeter (mm) For certain embodiments, the apertures have an average opening size (i.e., the largest dimension of the opening) of no greater than 0.5 centimeter (cm).

For certain embodiments, the porous substrates have a basis weight of at least 5 grams/meter$^2$. For certain embodiments, the porous substrates have a basis weight of no greater than 1000 grams/meter$^2$, and in some embodiments no greater than 200 grams/meter$^2$.

The porous substrates (i.e., backings) are preferably flexible yet resistant to tearing. For certain embodiments, the thickness of the porous substrates is at least 0.0125 millimeter (mm) For certain embodiments, the thickness of the porous substrates is no greater than 15 mm, and for certain embodiments no greater than 3 mm.

Materials of the backing or support substrate include a wide variety of materials including paper, natural or synthetic fibers, threads and yarns made from materials such as cotton, rayon, wool, hemp, jute, nylon, polyesters, polyacetates, polyacrylics, alginates, ethylene-propylene-diene rubbers, natural rubber, polyesters, polyisobutylenes, polyolefins (e.g., polypropylene polyethylene, ethylene propylene copolymers, and ethylene butylene copolymers), polyurethanes (including polyurethane foams), vinyls including polyvinylchloride and ethylene-vinyl acetate, polyamides, polystyrenes, fiberglass, ceramic fibers, and/or combinations thereof.

The backing can also be provided with stretch-release properties. Stretch-release refers to the property of an adhesive article characterized in that, when the article is pulled from a surface, the article detaches from the surface without leaving significant visible residue. For example, a film backing can be formed from a highly extensible and highly elastic composition that includes elastomeric and thermoplastic A-B-A block copolymers, having a low rubber modulus, a lengthwise elongation to break of at least 200%, and a 50% rubber modulus of not above 2,000 pounds/square inch (13.8 megapascals (MPa)). Such backings are described in U.S. Pat. No. 4,024,312 (Korpman). Alternatively, the backing can be highly extensible and substantially non-recoverable such as those described in U.S. Pat. No. 5,516,581 (Kreckel et al).

In certain embodiments, the coated substrates of the present invention are nonadherent, although it should be understood that an adhesive (e.g., a pressure sensitive adhesive) could be added to an article coated with the solution. As used herein, the silver compositions of the present invention when coated on a substrate do not adhere significantly to wound tissue such that they do not cause pain and/or destruction of the wound tissue upon removal and display a 180° peel strength of less than 1 N/cm from steel, as described in U.S. Pat. App. Pub. No. 2005/0123590.

In certain embodiments, substrates coated with the silver composition can be covered on one or both sides by a permeable nonadherent outside layer to reduce adhesion and attachment to the wound. The nonadherent layer can be attached to the substrate, such as by coating or laminating. Alternatively, the coated substrate can be enclosed within a nonadherent layer, such as sleeve. The nonadherent layer can be made from nonadherent woven or nonwoven fabrics such as nylon or perflourinated-material coatings on cotton gauze. The nonadherent layer prevents attachment of materials from the enclosed silver coated substrate. At the same time, the nonadherent layer does not adversely affect the sustained release of silver from the coated substrate.

In another embodiment, the backing or support substrate can be composed of nonadherent material. For example, a nonadherent hydrophilic polymer can be used as the backing or support material, or coated on a permeable porous substrate, as described in U.S. Pat. Pub. Nos. 2004/0180093, 2005/0123590, and 2005/0124724.

If desired, the coated substrate can be covered with two protective films (for example, thin polyester films). These films optionally may include a nonstick treatment and can function to facilitate extraction from a package and in handling the article. If desired, the coated substrate can be cut into individual compresses, of sizes suitable for the use, packaged in sealed sachets, and sterilized.

Pressure sensitive adhesives used in medical articles can be used in articles of the present invention. That is, a pressure sensitive adhesive material could be applied to the article of this invention, for example, around the periphery, to adhere the article to the skin.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Test Protocols

Volatile Organic Content

Volatile organic content (VOC) can be determined using ASTM D 2369-03. Three pouches were placed in a constant temperature, constant humidity (CTH) room (50% RH 23° C.) for 48 hours (hrs). Six samples were punched out with an 8.9 cm by 8.9 cm die punch for each pouch material. Each sample was weighed with a Mettler balance. Samples were placed polyethylene-side-up on aluminum trays and put in a forced air oven at 110±5° C. for 60 minutes (min) Samples were re-equilibrated in the CTH room for 48 hours and then reweighed.

Color Change

Color change was evaluated by visual ranking under fluorescent lighting (Philips, F32T8/TL735, Universal/Hi-Vision, E4). Samples were compared to color standards and given a rating based on that visual comparison. Color change was the difference in ratings obtained by subtracting the initial rating from the rating after treatment. Positive ratings represent a darkening in appearance and negative ratings represent a lightening in appearance.

Samples having color ratings (1-10) of the silver coated cotton samples were also measured using a Minolta Chroma Meter (CR-300, manufactured by Konica Minolta Photo Imaging U.S.A., Inc., Mahwah, N.J.) and gave the following results.

TABLE 1

Color Ratings and Measured Color

| Visual color rating | CIE Tristimulus values | | |
|---|---|---|---|
| | X | Y | Z |
| White standard | 92.98 | 94.95 | 108.54 |
| 1 | 71.9 | 72.97 | 52.43 |
| 3 | 59.74 | 59.48 | 33.84 |
| 4 | 50.77 | 50.00 | 23.68 |
| 5 | 41.92 | 39.87 | 23.07 |
| 7 | 28.88 | 26.82 | 18.78 |
| 8 | 26.90 | 24.81 | 17.22 |
| 10 | 26.4 | 24.88 | 19.42 |

Silver Measurements

Total Silver

Silver content of dressing was measured using EPA Procedure, EPA 6010B with ICP-AES detection.

Dressing Silver Ion Release

Silver ion release from dressing after 30 minutes immersion in distilled water was determined using an Ag ion selective electrode (Orion, available VWR International, Batavia, Ill.). Two 3.175 cm diameter discs were cut from the web, weighed, and placed in 98 milliliter (mL) of distilled water and 2 mL of 5M $NaNO_3$ was added to the amber bottle. The bottle was capped with a TEFLON lined lid and placed on a jar roller. After 30 minutes an ion selective electrode and double junction reference electrode were placed in the solution. The temperature was 21.2° C. The voltage across the electrodes was measured. A standard curve was determined by plotting log (silver ion concentration) versus millivolts (mV) for two standards, 1 microgram (μg) $Ag^+$/mL and 10 μg $Ag^+$/mL and using this curve to determine sample silver ion release by converting mV to silver ion concentration.

Substrate Anion Content

Anion content of the substrates was made using the following procedure. Extraction: The samples were weighed into 50 mL polypropylene centrifuge tubes, with 25 mL of 18 MΩ water pipetted. The samples were extracted for 24 hours at room temperature, at which time the cotton was removed. The sample was analyzed in triplicate with triplicate blanks using Ion Chromotography (IC).

IC: Solutions were transferred to 0.7 mL autosampler vials. Next, one 30 μL aliquot was injected from each autosampler vial into a DIONEX DX500 ion chromatograph using an AS3500 autosampler. The DIONEX chromatograph used a GP40 Gradient Pump and EG40 Eluent Generator to establish an eluent (gradient KOH 10-54 mM in 18 MΩ water) flow rate of 1 mL per minute. A conductivity detector (ED40), self-regenerating suppressor and columns AS18 (analytical) and AG18 (guard) were used. Concentration of extractable anions in units of parts per million (ppm, μg/g) were determined using standard solutions to calibrate the system for fluoride, acetate, formate, chloride, sulfate, bromide nitrate and phosphate.

Various substrates were evaluated for anion content before coating with silver salts. The anion content was determined using ion chromatography by the procedure described above gave the results in Table 2.

TABLE 2

Concentration of extractable anions in units of parts per million (ppm, µg/g).

| Sample | Fluoride | Acetate | Formate | Chloride | Sulfate | Bromide | Nitrate | Phosphate |
|---|---|---|---|---|---|---|---|---|
| Spuntech Cotton | 2 (±1) | 31.3 (±0.3) | 32 (±2) | 588 (±6) | 124 (±2) | 1.2 (±0.2) | 11.8 (±0.4) | ND <10 ppm |
| Unitika Cotton-COTTOASE | 0.9 (±0.3) | 5.7 (±0.6) | 11.5 (±0.3) | 6.9 (±0.1) | 11.0 (±2) | 3.4 (±0.4) | 9.7 (±1.0) | ND <10 ppm |
| Example 4 non-woven | 1.7 (±0.2) | 11.7 (±1.2) | 42 (±2) | 44.5 (±0.6) | 30.8 (±0.9) | 4.2 (±0.8) | 5.9 (±0.7) | ND <10 ppm |
| Nisshinbo Cotton | 0.28 (±0.02) | 32 (±4) | ND <1 ppm | 42 (±3) | 23.8 (±0.7) | 0.9 (±0.2) | 13.5 (±3.6) | 22.9 (±0.2) |

TABLE 3

MATERIALS

| DESIGNATION | DESCRIPTION | SOURCE/ADDRESS |
|---|---|---|
| P-1 | Non-peelable pouch<br>Top: Paper/LDPE (low density polyethylene)/aluminum/adhesive/LDPE<br>Bottom: Paper/LDPE/aluminum/adhesive/LDPE<br>VOC content 166 mg/m² | Pheonix Healthcare Products, LLC, Milwaukee, WI |
| To-1 | Peelable Foil pouch<br>Top: TPC-0765B PET/LDPE/Foil/Ionomer<br>Bottom: TPC-0760B PET/LDPE/Foil/LDPE/Peelable Sealant<br>VOC content 23 mg/m² | Tolas Health Care Packaging, Feasterville, PA |
| To-2 | Non-Peelable Pouch Polyester/LDPE/Foil/Ionomer<br>Top: TPC-0765B PET/LDPE/Foil/Ionomer<br>Bottom: TPC-0765B PET/LDPE/Foil/Ionomer<br>VOC content 15 mg/m² | Tolas Health Care Packaging, Feasterville, PA |
| Te-1 | Peelable Foil Pouch<br>Top: PET/White Opaque PP/Foil/PE<br>Bottom: PET/White Opaque PP/Foil/Peelable PE<br>VOC content 25 mg/m² | Technipaq; manufactured by Technipaq Inc., Crystal Lake, IL |
| Te-2 | Non-Peelable Foil Pouch<br>Top: PET/White Opaque PP/Foil/PE<br>Bottom: PET/White Opaque PP/Foil/PE<br>VOC content 22 mg/m² | Technipaq; manufactured by Technipaq Inc., Crystal Lake, IL |
| V-1 | Peelable Pouch<br>Top: Paper/LDPE/aluminum/adhesive/LDPE<br>Bottom: Paper/LDPE/aluminum/adhesive/LDPE/Full Peel Coating<br>VOC content 258 mg/m² | VP Group, Feuchtwangen, Germany |
| ACC | Activated carbon canister | SorbiCap; Multisorb Technologies, Inc. Buffalo, NY; part number 02-01803BG02 |

Example 1

Silver Sulfate Coated High Anion Containing Cotton Substrate

A silver sulfate coating solution was made by mixing silver sulfate (Colonial Metals Inc., Elkton, Md.) and water to make a 0.1333 gram (g or gm) AgSO₄ per 100 grams water solution. Spunlaced 100% cotton web (50 g/m²; 30.48 cm wide, manufactured by Spuntech Industries, Upper Tiberius, Israel) was coated with a slot die. The pump speed was 316 mL/min. The coated web was dried at 356° F. (180° C.). The oven length was 15.24 meters (m). The web speed was 3.048 m/min. The dried web was golden yellow. It was rolled up and placed in a heat sealable foil pouch. There was 4.7 mg total silver per gram dressing (Method: EPA 6010B using ICP-AES). Silver ion release was determined to be 4.2 milligrams (mg) Ag⁺/g dressing by the method defined.

Dressings were die cut and placed into the various packaging materials at a water activity=0.5 and the package heat sealed. The packaged silver dressings were electron beam irradiated at 30 kGy or gamma irradiated at 38 kGy. The samples were stored at room temperature for 1 to 8 weeks before evaluating color change. Table 4 has the results of those evaluations.

TABLE 4

Color change of Example 1.

| Treatment | Time after Treatment (weeks) | Pouch Material | | | | |
|---|---|---|---|---|---|---|
| | | P-1 | Te-1 | Te-2 | To-1 | To-2 |
| E-beam | 1 | 1* | 0 | 1 | 0 | 0.5 |
| E-beam | 8 | 0.5* | 1 | 1 | 0.5 | 1 |
| Gamma | 1 | 1* | 1* | 2 | 1 | 0.5 |
| Gamma | 8 | 2* | 1* | 2* | 2* | 2* |

*indicates that the post irradiation dressing was not homogenous in color due to either streaks or edge whitening; pre-irradiation color = 4

Example 2

Silver Sulfate Coated Low Anion Containing Cotton Substrate

Example 2 dressing was made as in Example 1 except that the spunlaced 100% cotton web was manufactured by Unitika Ltd., Osaka, Japan; under the trade designation COTTOASE, 280 millimeters (mm) wide; grams per square meter (50 gm/m²). This resulted in a dressing with 5.5 mg total silver per gram dressing (Method: EPA 6010B using ICP-AES) and a silver ion release of 3.6 mg Ag$^+$/g dressing was measured by the method in the Test Protocols. The dried dressing was yellow in color.

Dressings were die cut and placed into the various packaging materials at a water activity=0.5 and the package heat sealed. The packaged silver dressings were electron beam irradiated at 30 kGy or gamma irradiated at 38 kGy. The samples were stored at room temperature for 1 to 8 weeks before evaluating color change. Table 5 has the results of those evaluations.

TABLE 5

Color change of Example 2.

| Treatment | Time after Treatment (weeks) | Pouch Material | | | | |
|---|---|---|---|---|---|---|
| | | P-1 | Te-1 | Te-2 | To-1 | To-2 |
| E-beam | 1 | 0* | 0 | 0 | 0 | 0 |
| E-beam | 8 | −0.5* | 0 | 0.5 | 0.5 | 0 |
| Gamma | 1 | −0.5* | 1 | 1* | 2* | 0* |
| Gamma | 8 | −0.5* | 2* | 3* | 1* | 1* |

*indicates that the post irradiation dressing was not homogenous in color due to either streaks or edge whitening; pre-irradiation color = 3.

Example 3

Silver Sulfate Coated Low Anion Containing Cotton Substrate

Example 3 dressing was prepared as in Example 2 except that the drying temperature was 175° F. (79° C.). The dried silver sulfate coated cotton was white. There was 5.3 mg total silver per gram dressing (Method: EPA 6010B using ICP-AES) and the dressing had a silver ion release of 3.5 mg Ag$^+$/g dressing measured by the method in the Test Protocol. Dressings were die cut and placed into the various packaging materials at a water activity=0.5 and an activated carbon canister (ACC) insert was then added and the package heat sealed, packaging with dressing and without insert were also prepared. The packaged silver dressings were electron beam irradiated at 30 kGy or gamma irradiated at 38 kGy. The samples were stored at room temperature for 1 to 8 weeks before evaluating color change. The table shows the effect that the activated carbon present in the packaging has on the white Example 3 dressing material in various packaging materials.

TABLE 6

Color change of Example 3.

| Treatment | Insert | Time after Treatment (weeks) | Pouch Material | | | | |
|---|---|---|---|---|---|---|---|
| | | | P-1 | Te-1 | Te-2 | To-1 | To-2 |
| E-beam | None | 1 | 2* | 1.5 | 1.75 | 1 | 1.75 |
| E-beam | ACC | 1 | 0.75* | 0.5 | 0.5 | 0.5 | 0.5 |
| E-beam | None | 8 | 2* | 2 | 1.5 | 2 | 1 |
| E-beam | ACC | 8 | 1* | 0.5 | 0.5 | 1 | 0.5 |
| Gamma | None | 1 | 3.5* | 4* | 5.75* | 3 | 2.75 |
| Gamma | ACC | 1 | 0.75* | 1 | 0.75 | 0.75 | 0.75 |
| Gamma | None | 8 | 4* | 7* | 6* | 4* | 3* |
| Gamma | ACC | 8 | 1* | 0.5 | 1 | 1 | 0.5 |

*indicates that the post irradiation dressing was not homogenous in color due to either streaks or edge whitening; pre-irradiation color = 0

Example 4

Silver Sulfate Coated Multi Component Non-Woven

Silver sulfate coated on substrate was prepared as in Example 1 except that the web was a multicomponent web composed of TENCEL lyocell fiber/Type 254 CELBOND Bicomponent Fiber (PET/Copolyester, 2.0 denier): 95/5. The TENCEL lyocell fiber was manufactured by Lenzing AG. The Type 254 CELBOND Bicomponent Fiber was manufactured by Trevira, Spartanburg, S.C. There was 4.0 mg total silver per gram dressing (Method: EPA 6010B using ICP-AES). The silver ion release was measured as 2.5 mg Ag$^+$/g dressing by the test procedure described in the Test Protocol section.

The Example 4 dressings were not stable at 8 weeks in the P-1 packaging after electron beam or gamma irradiation at a water activity of 0.5 or at a water activity near 1.

The Example 4 dressings were stable at 50% RH or 100% RH in the To-1 packaging after electron beam.

Example 5

A silver sulfate coating solution was prepared by placing 0.289 g silver sulfate and 200 g distilled water in a glass bottle and capping the bottle and shaking at room temperature overnight. The resulting silver sulfate (approximately 1000 µg Ag/g) solution was coated on 100% cotton spunlaced non-woven mesh (COTTOASE, containing less than 20 ppm chloride) by transferring the solution by pipet to saturate the mesh that was contained in a polystyrene dish. Each piece of non-woven mesh (50 grams per square meter (gsm)) was treated with approximately 5.5 g of the solution on a 4.375 inch by 4.375 inch (11.11 cm×11.11 cm) piece of mesh. Approximately one gram of coating solution dripped off of the mesh before the mesh was suspended in the oven for drying. Some additional solution dripped off the mesh in the oven (estimated at 1 g). The coated mesh was dried in a forced air oven (Memmert Universal Oven, available from Wisconsin Oven Company, East Troy, Wis.) by heating at 170° C. for 12 minutes. The color of the samples after drying was golden yellow. The samples were placed in a foil pouch (Tolas Health Care Packaging, TPC-0765B/TPC-0760B construction) after drying and maintained at a relative humidity inside the pouch of less than 25%. Samples were also sealed in the foil pouch after drying and then exposed to gamma irradiation (32.9-33.5 kGy). The samples were removed from the pouches for color measurement at 2 and 29 days after irradiaton. Color CIE tristimulus values of the samples were measured using a Minolta Chroma Meter (CR-300, manufactured by Konica Minolta Photo Imaging U.S.A., Inc., Mahwah, N.J.). The results are shown in Table 7.

TABLE 7

Color of Example 5.

| Gamma irradiated | Days after Irradiation | Color of Sample | CIE Tristimulus Values | | |
|---|---|---|---|---|---|
| | | | X | Y | Z |
| No | — | golden yellow | 50.6 | 49.42 | 21.09 |
| Yes | 2 | golden yellow | 47.21 | 45.57 | 20.87 |
| Yes | 29 | golden yellow | 53.53 | 53.89 | 28.78 |

Example 6

Samples were prepared in same way as Example 5, except substrate was 100% cotton non-woven from Suntec Union, Japan (Nissinbo, AN20601050, 60 gsm). The color of the samples was a uniform golden yellow. The results are shown in Table 8.

TABLE 8

Color of Example 6.

| Gamma irradiated | Days after irradiation | Color of Sample | CIE Tristimulus Values | | |
|---|---|---|---|---|---|
| | | | X | Y | Z |
| No | — | golden yellow | 42.6 | 41.3 | 16.48 |
| Yes | 2 | golden yellow | 45.08 | 44.29 | 19.35 |
| Yes | 29 | golden yellow | 38.25 | 36.58 | 15.32 |

Example 7

Samples were prepared in the same way as Examples 5 and 6 and were then measured for silver release into a solution of distilled water and sodium nitrate using a silver ion selective electrode (Orion, available VWR International, Batavia, Ill.). Sodium nitrate is used as an ionic strength adjustor. The release was measured as described in the Test Protocol Section. The results of these measurements are in Table 9.

TABLE 9

Silver Ion Release.

| Example Number | Gamma irradiated | Days after irradiation | Color of Sample | Silver Release mg Ag+/g sample in 30 minutes |
|---|---|---|---|---|
| 5 | No | — | golden yellow | 7.9 |
| 5 | Yes | 2 | golden yellow | 5.7 |
| 5 | Yes | 29 | golden yellow | 6.6 |
| 6 | No | — | golden yellow | 4.1 |
| 6 | Yes | 2 | golden yellow | 4.0 |
| 6 | Yes | 29 | golden yellow | 3.5 |

Example 8

A 40 gram/m$^2$ spunlaced 100% cotton non-woven substrate was dip coated in a continuous manner into an approximately saturated solution of silver sulfate, squeezed to remove excess coating solution, and then dried at approximately 175° C. The resulting coated substrate contained 6 mg total silver per gram substrate and was golden yellow in color. Four-inch by 8-inch (10 cm×20 cm) samples were cut from the coated substrate, and then folded into 4-inch×4-inch (10 cm×10 cm) two-ply samples. These two-ply samples were then placed into porous packaging (5.75"×9.75" (14.6 cm×24.8 cm) unprinted Chevron peel pouch; uncoated TYVEK 1073B/TPF-0501A construction; Tolas Health Care Packaging, Feasterville, Pa.; containing a VOC content of less than 50 mg/m$^2$), and the package was heat sealed. Some of these packaged samples were then e-beam irradiated at 21.5-28.9 kGy by Steris Isomedix in Libertyville, Ill., and some of these packaged samples were not irradiated.

Three packaged samples (either e-beam irradiated or not) were then placed into a second non-porous package (custom made from Technipaq Inc. Crystal Lake, Ill.; zipper pouch with bottom gusset/unprinted; 12.5-inch×10.5-inch×2.5-inch OD (31.8 cm×26.7 cm×6.4 cm); 60 ga Biax Orientated Nylon/A/0.00035 Foil/A/3.5 mil (0.009 cm) Linear Low Density Polyethylene construction) along with one 3.0 gram activated carbon/silica gel (50/50) absorbent sachet (Multisorb Technologies, Inc., Buffalo, N.Y.). After the addition of the packaged samples and the absorbent sachet, the second non-porous package was heat sealed, and then aged at room temperature.

The samples were removed from both pouches for color measurement at specified aging times as described in Table 10. Color CIE tristimulus values of the samples were measured using a Minolta Chroma Meter (CR-300, manufactured by Konica Minolta Photo Imaging U.S.A., Inc., Mahwah, N.J.). Results are shown in Table 10.

TABLE 10

Color of Example 8.

| E-beam irradiated | Months of Aging study | Color of Sample | CIE Tristimulus Values | | |
|---|---|---|---|---|---|
| | | | X | Y | Z |
| No | initial | golden yellow | 57.72 | 57.58 | 36.63 |
| No | initial | golden yellow | 54.79 | 54.43 | 31.85 |
| No | initial | golden yellow | 56.20 | 56.00 | 33.03 |
| Yes | initial | golden yellow | 52.16 | 51.41 | 29.58 |
| Yes | initial | golden yellow | 58.23 | 58.10 | 35.88 |
| Yes | initial | golden yellow | 56.14 | 55.85 | 32.53 |
| No | 3 | golden yellow | 54.65 | 54.24 | 32.58 |
| No | 3 | golden yellow | 58.66 | 58.71 | 38.30 |
| No | 3 | golden yellow | 58.04 | 58.07 | 37.77 |
| Yes | 3 | golden yellow | 56.27 | 55.99 | 35.65 |
| Yes | 3 | golden yellow | 59.11 | 59.10 | 35.92 |
| Yes | 3 | golden yellow | 58.37 | 58.27 | 35.92 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A packaged antimicrobial article, comprising:
   an antimicrobial article comprising a silver nitrate oxidizable substrate, wherein the substrate has disposed thereon silver sulfate and silver metal in the zero-valent state; and
   packaging having the antimicrobial article sealed therein;
   wherein the antimicrobial article is color stable during and after irradiation; and
   wherein the packaging comprises material having a volatile organic content of no greater than 100 mg per square meter;
   wherein if the antimicrobial article includes a stabilizing agent, the stabilizing agent is present in an amount of less than 100 parts per million; and
   wherein the silver sulfate concentration on the substrate ranges from 0.001 mg/cm$^2$ to 5 mg/cm$^2$ and the total amount of stabilizing agent is less than the total amount of silver.

2. The packaged article of claim 1 which has a whitish color and activated carbon sealed with the article within the packaging.

3. The packaged article of claim 1 wherein the substrate comprises a cellulosic material.

4. The packaged article of claim 3 wherein the substrate comprises cotton.

5. The packaged article of claim 1 wherein the substrate is a nonwoven gauze, a woven gauze, a porous film, a nonporous film, a knitted fabric, foam, or a hydrocolloid.

6. The packaged article of claim 1 wherein the antimicrobial article is maintained in an environment of no more than 50% RH at room temperature.

7. The packaged article of claim 6 wherein the antimicrobial article is maintained in an environment of no more than 30% RH at room temperature.

8. The packaged article of claim 1 wherein the substrate has disposed thereon silver compounds other than silver sulfate.

9. The packaged article of claim 8 wherein the silver compounds are selected from the group consisting of silver oxide, silver nitrate, silver acetate, silver citrate, silver chloride, silver lactate, silver phosphate, silver stearate, silver thiocyanate, silver carbonate, silver saccharinate, silver anthranilate, silver benzoate, and combinations thereof.

10. The packaged article of claim 1 wherein the packaging comprises material having an oxygen permeability of less than 0.01 cubic centimeter per 645 square centimeters per 24 hours.

11. The packaged article of claim 1 wherein the packaging comprises material having a moisture vapor transmission rate of less than 0.01 gram per 645 square centimeters per 24 hours.

12. A packaged antimicrobial article, comprising:
an antimicrobial article comprising a cellulosic substrate, wherein the substrate has disposed thereon silver sulfate and silver metal in the zero-valent state; and
packaging having the antimicrobial article sealed therein;
wherein the antimicrobial article is color stable during and after irradiation; and
wherein the packaging comprises material having a volatile organic content of no greater than 100 mg per square meter;
wherein if the antimicrobial article includes a stabilizing agent, the stabilizing agent is present in an amount of less than 100 parts per million; and
wherein the silver sulfate concentration on the substrate ranges from 0.001 $mg/cm^2$ to 5 $mg/cm^2$ and the total amount of stabilizing agent is less than the total amount of silver.

13. The packaged article of claim 12 wherein the substrate comprises cotton.

14. A packaged antimicrobial article, comprising:
an antimicrobial article comprising a silver nitrate oxidizable substrate, wherein the substrate has disposed thereon silver sulfate and silver metal in the zero-valent state; and
packaging having the antimicrobial article sealed therein;
wherein the antimicrobial article is color stable during and after irradiation; and
wherein the packaging comprises material having a volatile organic content of no greater than 100 mg per square meter;
wherein if the antimicrobial article includes a stabilizing agent, the stabilizing agent is present in an amount of less than 100 parts per million (ppm);
wherein the silver sulfate concentration on the substrate is at least 167 ppm.

15. The packaged antimicrobial article of claim 14 wherein the silver sulfate concentration on the substrate is 167 ppm to $1.25 \times 10^6$ ppm.

16. A packaged antimicrobial article, comprising:
an antimicrobial article comprising a cellulosic substrate, wherein the substrate has disposed thereon silver sulfate and silver metal in the zero-valent state; and
packaging having the antimicrobial article sealed therein;
wherein the antimicrobial article is color stable during and after irradiation; and
wherein the packaging comprises material having a volatile organic content of no greater than 100 mg per square meter;
wherein if the antimicrobial article includes a stabilizing agent, the stabilizing agent is present in an amount of less than 100 parts per million (ppm);
wherein the silver sulfate concentration on the substrate is at least 167 ppm.

17. The packaged antimicrobial article of claim 16 wherein the silver sulfate concentration on the substrate is 167 ppm to $1.25 \times 10^6$ ppm.

18. A packaged antimicrobial article, comprising:
an antimicrobial article comprising a silver nitrate oxidizable substrate, wherein the substrate has disposed thereon silver sulfate and silver metal in the zero-valent state; and
packaging having the antimicrobial article sealed therein;
wherein the antimicrobial article is color stable during and after irradiation; and
wherein the packaging comprises material having a volatile organic content of no greater than 100 mg per square meter;
wherein if the antimicrobial article includes a stabilizing agent, the stabilizing agent is present in an amount of less than 100 parts per million; and
wherein the silver sulfate concentration on the substrate ranges from 0.001 $mg/cm^2$ to 5 $mg/cm^2$, the substrate basis weight is 5 $g/m^2$ to 1000 $g/m^2$ and the total amount of stabilizing agent is less than the total amount of silver.

19. The packaged antimicrobial article of claim 18 wherein the substrate basis weight is 5 $g/m^2$ to 200 $g/m^2$.

20. The packaged antimicrobial article of claim 19 wherein the substrate basis weight is 40 $g/m^2$ to 60 $g/m^2$.

21. A packaged antimicrobial article, comprising:
an antimicrobial article comprising a cellulosic substrate, wherein the substrate has disposed thereon silver sulfate and silver metal in the zero-valent state; and
packaging having the antimicrobial article sealed therein;
wherein the antimicrobial article is color stable during and after irradiation; and
wherein the packaging comprises material having a volatile organic content of no greater than 100 mg per square meter;
wherein if the antimicrobial article includes a stabilizing agent, the stabilizing agent is present in an amount of less than 100 parts per million;
wherein the silver sulfate concentration on the substrate ranges from 0.001 $mg/cm^2$ to 5 $mg/cm^2$, the substrate basis weight is 5 $g/m^2$ to 1000 $g/m^2$ and the total amount of stabilizing agent is less than the total amount of silver.

22. The packaged antimicrobial article of claim 21 wherein the substrate basis weight is 5 $g/m^2$ to 200 $g/m^2$.

23. The packaged antimicrobial article of claim 22 wherein the substrate basis weight is 40 $g/m^2$ to 60 $g/m^2$.

* * * * *